US008565926B2

(12) United States Patent
Luc et al.

(10) Patent No.: US 8,565,926 B2
(45) Date of Patent: *Oct. 22, 2013

(54) MULTIPLE VOLATILE MATERIAL DISPENSING DEVICE AND OPERATING METHODOLOGIES THEREFORE

(75) Inventors: Tai P. Luc, Oak Creek, WI (US); Kenneth W. Michaels, Spring Grove, IL (US); Megan L. Polzin, Sturtevant, WI (US); Bhavesh Shah, Kenosha, WI (US)

(73) Assignee: S.C. Johnson & Son, Inc., Racine, WI (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/552,448

(22) Filed: Jul. 18, 2012

(65) Prior Publication Data

US 2012/0283884 A1 Nov. 8, 2012

Related U.S. Application Data

(63) Continuation of application No. 12/790,243, filed on May 28, 2010, now Pat. No. 8,255,089.

(51) Int. Cl.
*G05D 7/00* (2006.01)
*G05D 11/00* (2006.01)
*G07F 11/00* (2006.01)
*B67D 1/00* (2006.01)
*B67D 7/14* (2010.01)
*G08B 21/00* (2006.01)

(52) U.S. Cl.
USPC ............. 700/283; 700/231; 221/9; 221/10; 221/15; 222/25; 222/52; 222/68; 340/5.9; 340/540

(58) Field of Classification Search
USPC ........ 222/94–95, 136, 145.5, 402.21–402.25, 222/1, 25, 52, 68; 700/231, 283; 221/9–10, 221/15, 245; 340/5, 9, 540
See application file for complete search history.

(56) References Cited

U.S. PATENT DOCUMENTS

| 3,677,441 | A | | 7/1972 | Nixon, Jr. et al. |
| 4,792,062 | A | | 12/1988 | Goncalves |
| 4,969,579 | A | | 11/1990 | Behar |
| 5,002,048 | A | | 3/1991 | Makiej, Jr. |
| 5,007,419 | A | | 4/1991 | Weinstein et al. |
| 5,234,162 | A | | 8/1993 | Sullivan |
| 5,339,874 | A | * | 8/1994 | Cragun ............................. 141/9 |
| 5,437,267 | A | | 8/1995 | Weinstein et al. |

(Continued)

FOREIGN PATENT DOCUMENTS

| EP | 0245172 A1 | 11/1987 |
| EP | 0279727 A1 | 8/1988 |

(Continued)

*Primary Examiner* — Ramesh Patel

(57) ABSTRACT

A dispensing device includes first and second actuators that actuate first and second containers, respectively, to dispense volatile material therefrom and a sensor for detecting an environmental condition. In a first period the first and second actuators are inactive, in a second period the first actuator actuates the first container at a first frequency to dispense volatile material therefrom, and in a third period the second actuator actuates the second container at a second frequency to dispense volatile material therefrom. If the sensor has detected the environmental condition, the first and/or second actuators actuate the first and/or second containers, respectively, during a fourth period at a third frequency.

18 Claims, 4 Drawing Sheets

(56) References Cited

U.S. PATENT DOCUMENTS

| | | |
|---|---|---|
| 5,565,148 A | 10/1996 | Pendergrass, Jr. |
| 6,036,108 A | 3/2000 | Chen |
| 6,189,810 B1 | 2/2001 | Nerushai et al. |
| 6,267,297 B1 | 7/2001 | Contadini et al. |
| 6,461,325 B1 | 10/2002 | Delmotte et al. |
| 6,540,155 B1 | 4/2003 | Yahav |
| 6,554,203 B2 | 4/2003 | Hess et al. |
| 6,644,507 B2 | 11/2003 | Borut et al. |
| 6,689,621 B2 * | 2/2004 | Merten et al. ............... 436/180 |
| 6,691,898 B2 | 2/2004 | Hurray et al. |
| 6,696,298 B2 * | 2/2004 | Cook et al. .................. 506/40 |
| 6,712,287 B1 | 3/2004 | Le Pesant et al. |
| 6,790,408 B2 | 9/2004 | Whitby et al. |
| 6,877,636 B2 | 4/2005 | Speckhart et al. |
| 6,916,584 B2 * | 7/2005 | Sreenivasan et al. ........... 430/22 |
| 6,942,469 B2 * | 9/2005 | Seale et al. ................ 417/413.1 |
| 7,011,795 B2 | 3/2006 | Thompson et al. |
| 7,013,888 B2 | 3/2006 | Hughes et al. |
| 7,223,361 B2 | 5/2007 | Kvietok et al. |
| 7,249,719 B2 | 7/2007 | He et al. |
| 7,357,158 B2 * | 4/2008 | Yerby et al. ................... 141/9 |
| 7,407,065 B2 | 8/2008 | Hooks et al. |
| 7,481,380 B2 | 1/2009 | Kvietok et al. |
| 7,665,673 B2 | 2/2010 | Hagleitner |
| 7,798,366 B2 | 9/2010 | Hoshino |
| 7,893,829 B2 | 2/2011 | Sipinski et al. |
| 7,959,041 B2 * | 6/2011 | Miller et al. ............ 222/402.16 |
| 8,074,640 B2 * | 12/2011 | Davies et al. ............ 128/200.14 |
| 8,255,089 B2 * | 8/2012 | Luc et al. .................... 700/283 |
| 2002/0058595 A1 | 5/2002 | Kaiser |
| 2002/0066756 A1 | 6/2002 | Kinsman |
| 2002/0068009 A1 | 6/2002 | Laudamiel-Pellet et al. |
| 2002/0068010 A1 | 6/2002 | Laudamiel-Pellet et al. |
| 2002/0074357 A1 | 6/2002 | Karr et al. |
| 2002/0090737 A1 * | 7/2002 | Levin et al. .................. 436/180 |
| 2002/0130574 A1 * | 9/2002 | Borut et al. .................. 222/645 |
| 2004/0007787 A1 | 1/2004 | Kvietok et al. |
| 2004/0009103 A1 | 1/2004 | Westring |
| 2004/0025865 A1 * | 2/2004 | Nichols et al. ........... 128/200.14 |
| 2004/0028551 A1 | 2/2004 | Kvietok et al. |
| 2004/0033171 A1 | 2/2004 | Kvietok et al. |
| 2004/0050383 A1 * | 3/2004 | Cox et al. ............... 128/200.14 |
| 2004/0118396 A1 | 6/2004 | Hughes et al. |
| 2004/0265164 A1 | 12/2004 | Woo et al. |
| 2005/0139624 A1 | 6/2005 | Hooks et al. |
| 2005/0147523 A1 | 7/2005 | Laudamiel-Pellet et al. |
| 2005/0147539 A1 | 7/2005 | Laudamiel-Pellet et al. |
| 2005/0211790 A1 | 9/2005 | Kvietok et al. |
| 2006/0049278 A1 | 3/2006 | Hoshino |
| 2006/0097066 A1 | 5/2006 | Kvietok et al. |
| 2006/0121844 A1 * | 6/2006 | Sparks, II .................. 454/337 |
| 2006/0171091 A1 * | 8/2006 | Seale et al. ................... 361/160 |
| 2006/0261179 A1 * | 11/2006 | Davies et al. .................. 239/34 |
| 2007/0063072 A1 | 3/2007 | Ganan Calvo et al. |
| 2007/0095941 A1 | 5/2007 | Gorres |
| 2007/0160492 A1 | 7/2007 | Spector |
| 2007/0280653 A1 | 12/2007 | Viera |
| 2008/0061082 A1 | 3/2008 | Anderson et al. |
| 2008/0069725 A1 | 3/2008 | Kvietok et al. |
| 2008/0156896 A1 | 7/2008 | Anderson et al. |
| 2008/0210772 A1 | 9/2008 | Pearce et al. |
| 2009/0020560 A1 | 1/2009 | Kraus |
| 2009/0108021 A1 | 4/2009 | Hansen et al. |
| 2009/0185950 A1 | 7/2009 | Woo et al. |
| 2009/0185952 A1 | 7/2009 | Bankers et al. |
| 2009/0218413 A1 | 9/2009 | Withers |
| 2009/0293733 A1 * | 12/2009 | Martin et al. ................. 99/280 |
| 2009/0302056 A1 | 12/2009 | Butler |
| 2009/0309717 A1 | 12/2009 | Sipinski et al. |
| 2009/0314849 A1 | 12/2009 | Litten-Brown et al. |
| 2009/0321475 A1 * | 12/2009 | Schultz ........................ 222/52 |
| 2010/0025427 A1 * | 2/2010 | Chiou et al. ..................... 222/1 |
| 2010/0038379 A1 | 2/2010 | Butler et al. |
| 2010/0294852 A1 * | 11/2010 | Banco et al. ..................... 239/6 |
| 2011/0278322 A1 * | 11/2011 | Reynolds et al. ............... 222/1 |
| 2013/0001244 A1 * | 1/2013 | Wegelin et al. ................. 222/1 |
| 2013/0068788 A1 * | 3/2013 | Gasper et al. ................. 222/63 |

FOREIGN PATENT DOCUMENTS

| | | |
|---|---|---|
| EP | 0580572 B1 | 11/1997 |
| EP | 1595822 A1 | 11/2005 |
| EP | 1997747 A2 | 12/2008 |
| EP | 2006219 A1 | 12/2008 |
| EP | 2006220 A1 | 12/2008 |
| EP | 2070841 A1 | 6/2009 |
| EP | 2133103 A1 | 12/2009 |
| EP | 1737760 B1 | 3/2010 |
| GB | 2337203 B | 11/1999 |
| GB | 2337203 A | 12/2002 |
| WO | 92/16249 A1 | 10/1992 |
| WO | 01/26448 A1 | 4/2001 |
| WO | 01/92131 A1 | 12/2001 |
| WO | 2004/076312 A1 | 9/2004 |
| WO | 2005/095000 A2 | 10/2005 |
| WO | 2005/095000 A3 | 10/2005 |
| WO | 2005/095230 A1 | 10/2005 |
| WO | 2006/037823 A1 | 4/2006 |
| WO | 2006/084921 A1 | 8/2006 |
| WO | 2006/087514 A1 | 8/2006 |
| WO | 2006/110869 A1 | 10/2006 |
| WO | 2007/132140 A1 | 11/2007 |
| WO | 2008/037103 A1 | 4/2008 |
| WO | 2008/124958 A1 | 10/2008 |
| WO | 2008149065 A1 | 12/2008 |
| WO | 2009/060205 A1 | 5/2009 |
| WO | 2009060212 A2 | 5/2009 |

* cited by examiner

MULTIPLE VOLATILE MATERIAL DISPENSING DEVICE AND OPERATING METHODOLOGIES THEREFORE

CROSS REFERENCE TO RELATED APPLICATIONS

This application is a continuation of U.S. patent application Ser. No. 12/790,243, filed May 28, 2010.

REFERENCE REGARDING FEDERALLY SPONSORED RESEARCH OR DEVELOPMENT

Not applicable

SEQUENTIAL LISTING

Not applicable

BACKGROUND OF THE INVENTION

1. Field of the Invention

The present disclosure relates generally to volatile material dispensing devices and operating methodologies therefore and, more particularly, to such devices and methodologies that dispense multiple volatile materials.

2. Description of the Background

Volatile material dispensing devices come in a variety of different forms. Some dispensing devices require only only ambient airflow to disperse a liquid volatile material therefrom, e.g., from a wick extending from a volatile material container. Other devices are battery-powered or receive household power via a plug extending from the device. Some such battery-powered devices include a heating element for heating a volatile material to promote vaporization thereof. Other devices employ a fan or blower to generate airflow to direct volatile material out of the device into the surrounding environment. Still other devices that dispense volatile materials utilize ultrasonic means to dispense the volatile materials therefrom. In yet another example, some dispensing devices are configured to automatically actuate an aerosol container containing a pressurized fluid to dispense the fluid therefrom.

In the past, various means have been utilized to dispense one or more volatile materials from a single device. Multiple volatile materials have been used, for example, to prevent habituation, which is a phenomenon that occurs when a person becomes used to a particular volatile material such that they no longer perceive that volatile material. Alternatively or in conjunction, multiple volatile materials have been used to provide environmental effects that can be customized by a user, e.g., to provide a first fragrance in the morning to gently encourage a user to awake from sleep and a second fragrance in the evening to calm the user before falling asleep.

Due, in part, to the variety of user preferences and needs for creating individualized environmental effects, there is an ever growing need for different volatile material dispensing devices to suit different users. Consequently, the present disclosure provides volatile material dispensers with different operating methodologies that may be preferred by some users over other devices.

SUMMARY OF THE INVENTION

In one example, a dispensing device includes first and second actuators adapted to actuate first and second containers, respectively, to dispense volatile material therefrom and a sensor for detecting an environmental condition. In a first period the first and second actuators are inactive, in a second period the first actuator actuates the first container at a first frequency to dispense volatile material therefrom, and in a third period the second actuator actuates the second container at a second frequency to dispense volatile material therefrom. If the sensor has detected the environmental condition, the first and/or second actuators actuate the first and/or second containers, respectively, during a fourth period at a third frequency.

In another example, a dispensing device includes first and second actuators adapted to actuate first and second containers, respectively, to dispense volatile material therefrom and a sensor for detecting an environmental condition. During a first period the first actuator actuates the first container for a first actuation sequence to dispense volatile material therefrom and during a second period the second actuator actuates the second container for a second actuation sequence to dispense volatile material therefrom. The first and second actuation sequences are performed only if the sensor has detected the environmental condition.

In yet another example, a dispensing device includes first and second actuators adapted to actuate first and second containers, respectively, to dispense volatile material therefrom. The first and second actuators actuate the first and second containers, respectively, to dispense volatile material therefrom during a twenty-four hour period that is divided into consecutive first, second, and third periods. During the first period the first and second actuators are inactive, during the second period the first actuator actuates the first container to dispense volatile material therefrom, and during the third period the second actuator actuates the second container to dispense volatile material therefrom.

Other aspects and advantages of the present invention will become apparent upon consideration of the following detailed description.

DETAILED DESCRIPTION OF THE DRAWINGS

Figure 1:
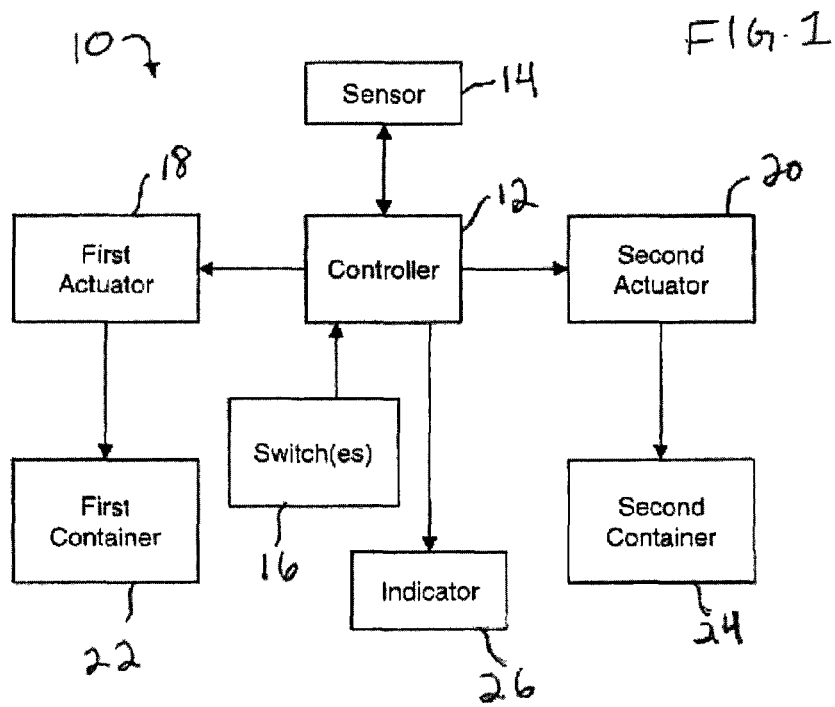
FIG. 1 is a block diagram of one embodiment of a volatile material dispensing device.

FIG. 1 illustrates a volatile material dispensing device 10 that includes a controller 12, a sensor 14, one or more switches or input devices 16, a first actuator 18, a second actuator 20, a first container 22, and a second container 24. The controller 12, which can be a microprocessor, an application specific integrated circuit, or any other combination of hardware and software components, is configured to activate/deactivate the sensor 14 and to receive inputs therefrom. For example, the sensor 14 may be an ambient light sensor, a motion sensor to detect motion or an attribute associated with motion, a chemical sensor for detecting a malodor and/or a volatile material, a pressure sensor, a thermal sensor, etc. Generally, the sensor 14 is configured to detect an environmental condition, such as, the presence of an individual, and to send a signal to the controller representative of the environmental condition. The controller is further coupled to switch(es) 16 to receive inputs therefrom, e.g., the switch(es) 16 can be used to turn the device 10 on and off, to set a time and date, to select a timing interval, to select an operating mode, etc., as would be apparent to one of skill in the art. Further, a power source (not shown), which may include, e.g., batteries, a connection to an electrical outlet, solar power, etc., may also be coupled to one or more of the components of the device 10 to power same.

The first and second actuators 18, 20 are coupled to and controlled by the controller 12 to actuate the first and second containers 22, 24, respectively, to dispense or spray volatile material therefrom. The actuators 18, 20 and containers 22, 24 may be any known combination designed to dispense volatile material. In one non-limiting example, the containers may include wicks extending therefrom and the actuators may be piezoelectric elements for atomizing fluid from the wicks or the actuators may be heaters and/or fans for actively dispersing fluid from the wicks. In another non-limiting example, the containers are aerosol containers and the actuators are configured to actuate a valve stem of the aerosol containers to dispense fluid therefrom. In addition, the first and second actuators 18, 20 need not be separate and distinct devices but may comprise portions of a single device that is configured to actuate both of the containers 22, 24, either at the same time or alternatively.

Further, the controller 12 may include memory for storing programming to control the operation of the device 10. In other embodiments, the controller 12 includes other components, such as, for example, timers and clocks, analog/digital converters, input/output interfaces, logic elements, etc., as would be apparent to one skilled in the art. Other modifications to the device 10 of FIG. 1 can be made without departing from the spirit of the present disclosure. For example, the device 10 may include fewer or additional components, such as, an indicator 26, which can be a display and/or one or more indicator lights, as would be apparent to one of skill in the art.

Figure 2:
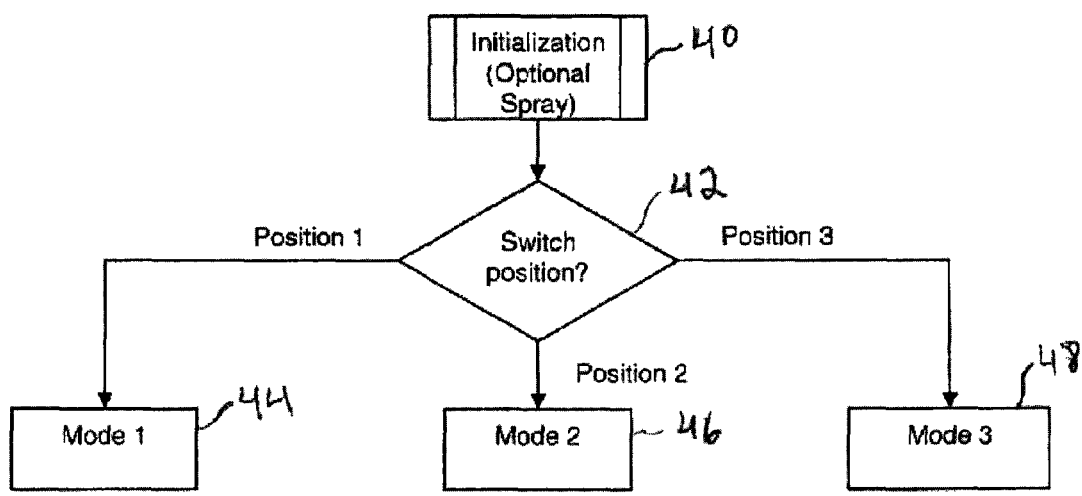
FIG. 2 is a flowchart that illustrates programming that may be executed by the device of FIG. 1 to operate in Mode 1, Mode 2, and/or Mode 3.

One embodiment of processes executed by hardware and/or software components of the controller 12 is illustrated in FIG. 2, which initiates at a block 40. Initialization by the block 40 occurs, e.g., when a power source is supplied to the device 10 by turning the switch 16 to an on position, by inserting batteries, or otherwise coupling power to the device, after which a start-up procedure may be performed. In one embodiment, the start-up procedure includes a short delay, such as, about five seconds, and an actuation of one or both of the containers 22, 24, to dispense volatile material. The initialization block 40 may further initialize the controller 12, e.g., by loading the current time. In other embodiments, the start-up procedure may be modified or even eliminated without departing from the spirit of the present disclosure. After the block 40, control passes to a decision block 42 that determines a position of a mode select switch, e.g., the switch 16 of FIG. 1, to determine whether the controller 12 will operate in Mode 1, Mode 2, or Mode 3 designated by blocks 44, 46, and 48, respectively. In other examples, the switch is not a physical switch and, instead, the controller 12 is merely programmed or otherwise designed to operate in one of the Modes. After the block 42 determines the selected operating mode, control passes to a respective block 44, 46, or 48.

Figure 3:
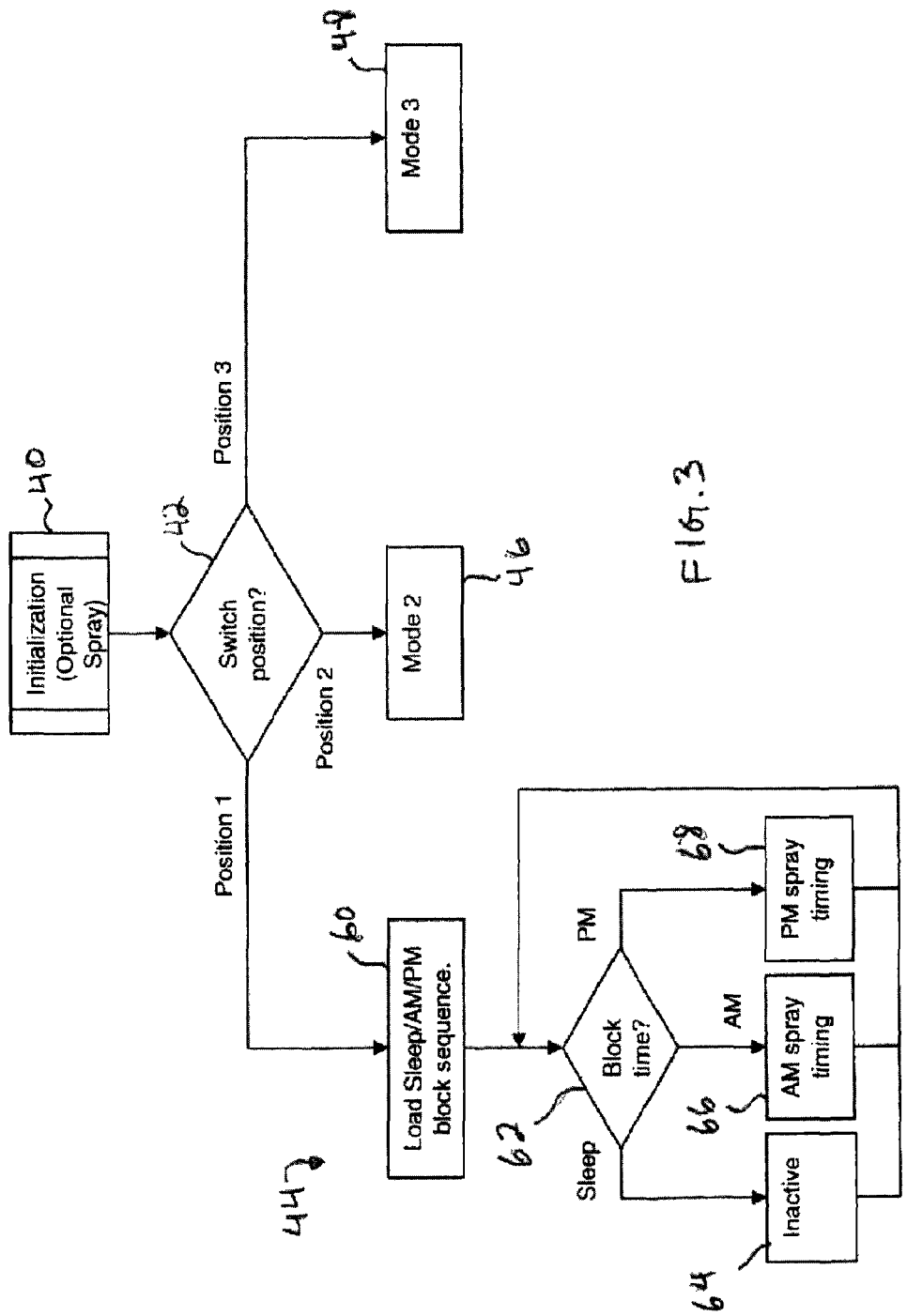
FIG. 3 is a flowchart that illustrates one embodiment of programming according to Mode 1 of FIG. 1.

Referring now to FIG. 3, Mode 1 begins at a block 60, which loads a Sleep/AM/PM block sequence. The block sequence can be loaded from internal or external memory coupled to the device 10 or can be set and adjusted by a user via one or more inputs or switches, e.g., the switches 16 of FIG. 1. In the present embodiment, Mode 1 is programmed to divide a twenty-four hour day into three time periods with three spray timings or sequences, e.g., Sleep, AM, and PM. In one non-limiting example, the Sleep sequence can be set to a time period when users are not expected to be awake or in a vicinity of the device 10, such as, between 12:00 AM and 6:00 AM, during which period the device is in an inactive state and no volatile is dispensed. The AM sequence can be set to a morning time period, e.g., between 6:01 AM and 3:00 PM, during which period the device 10 can be controlled to actuate the first container 22 to dispense volatile material according to an AM spray timing, e.g., one spray every twenty minutes. Further, the PM sequence can be set to a PM time period, e.g., between 3:01 PM and 11:59 PM, during which period the device 10 can be controlled to actuate the second container 24 to dispense volatile material according to a PM spray timing, e.g., one spray every twenty minutes.

Following the block 60, control passes to a block 62, which determines the current time period, e.g., the Sleep sequence time period between 12:00 AM and 6:00 AM, the AM sequence time period between 6:01 AM and 3:00 PM, or the PM sequence time period between 3:01 PM and 11:59 PM. In the current non-limiting example, if the current time period is the Sleep period, control passes to a block 64 and the device 10 is controlled according to the inactive state where no volatile is dispensed. If the current time period is the AM period, control passes to a block 66 and the device 10 is controlled according to the AM spray timing to dispense the volatile material from the first container 22 once every twenty minutes. Similarly, if the current time period is the PM period, control passes to a block 68 and the device 10 is controlled according to the PM spray timing to dispense volatile material from the second container 24 once every twenty minutes. Concurrently while executing the blocks 64, 66, 68, control loops to the block 62 to continually monitor the current time period and direct control to an appropriate block 64, 66, or 68, particularly, if there is a change in the current period.

Figure 4:
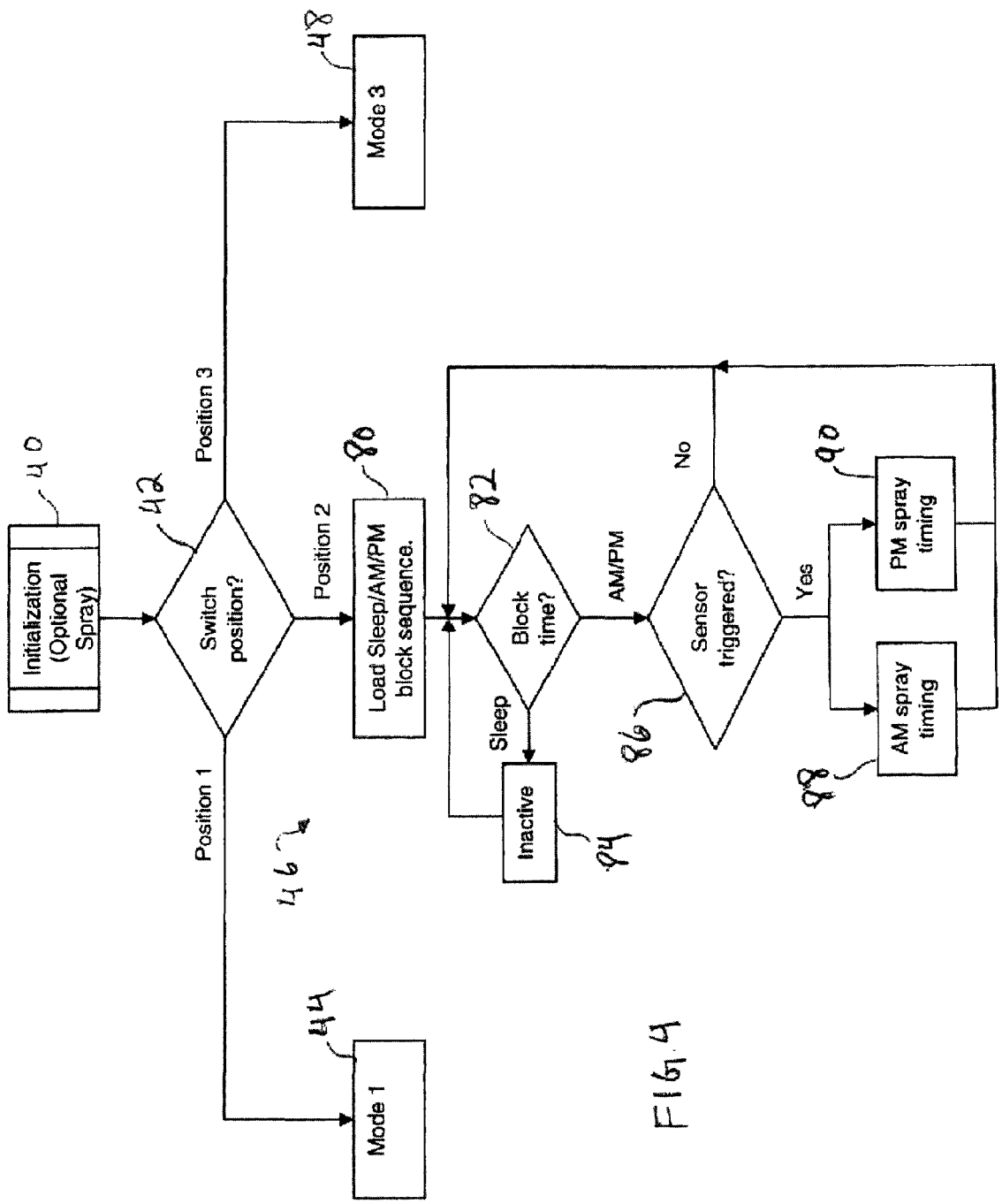
FIG. 4 is a flowchart that illustrates one embodiment of programming according to Mode 2 of FIG. 1.

Referring now to FIG. 4, Mode 2 begins at a block 80, which loads a Sleep/AM/PM block sequence, similarly to the block 60 of FIG. 3. For example, the Sleep/AM/PM block sequence loaded by the block 80 may include the same or different time periods and/or spray timings. In one non-limiting example, the Sleep sequence time period can be set to between 12:00 AM and 6:00 AM, during which the device 10 is in an inactive state and no volatile is dispensed. The AM sequence time period can be set to between 6:01 AM and 3:00 PM, during which the device 10 can be controlled to actuate the first container 22 according to an AM spray timing to dispense volatile material once every twenty minutes. Further, the PM sequence time period can be set to between 3:01 PM and 11:59 PM, during which the device 10 can be controlled to actuate the second container 24 according to a PM spray timing to dispense volatile material once every twenty minutes.

Following the block 80, control passes to a block 82 to determine the current time period, e.g., the Sleep sequence time period between 12:00 AM and 6:00 AM, the AM sequence time period between 6:01 AM and 3:00 PM, or the PM sequence time period between 3:01 PM and 11:59 PM. If the current time period is the Sleep period, control passes to a block 84 and the device 10 is controlled according to the inactive state where no volatile is dispensed. As shown in FIG. 4, after control passes to the block 84, control loops back to the decision block 82 to continually monitor the current time period. If the block 82 determines that the current time period is the AM or PM period, control passes to a block 86 to activate a sensor, e.g., the sensor 14 of FIG. 1, and to determine whether the sensor has been triggered. The sensor can be a motion sensor that is triggered by detecting motion, a pressure sensor that is triggered by a user pressing on the pressure sensor, or any other type of sensor that would be apparent to one of ordinary skill. If the sensor has not been triggered, control returns to the block 82 to continually monitor the current time period. However, if the sensor has been triggered, control passes to blocks 88, 90 depending on the current time period. More particularly, if the current time period is the AM period, control passes to the block 88 and the device 10 is controlled according to the AM spray timing to dispense the volatile material from the first container 22 once every twenty minutes. If the current time period is the PM period, control passes to the block 90 and the device 10 is controlled according to the PM spray timing to dispense volatile material from the second container 24 once every twenty minutes. Further, the blocks 88, 90 may provide an initial actuation of the containers 22, 24 immediately when the sensor is triggered or may actuate the containers after a brief delay.

Control may remain at the blocks 88, 90 for the duration of the respective time period before looping back to the block 82. Consequently, in the blocks 88, 90, control may monitor the current time period to determine whether the current period has elapsed. In the present example, control may monitor the current time period continuously or periodically after a lock out period following each actuation. In one non-limiting example, control may periodically determine the current time period after a twenty minute lockout period following each actuation. If the current period has elapsed, then control can immediately loop back to the block 82 and the block 86 can activate and monitor the sensor, as described above.

In another non-limiting example, control remains at the blocks 88, 90 for a period shorter than the AM or PM time period, e.g., two hours. In the present example, control loops back to the block 82 after remaining at the block 88 for two hours while the first actuator 18 is controlled to actuate the first container 22 to dispense volatile material every twenty minutes or at the block 90 for two hours while the second actuator 20 is controlled to actuate the second container 24 to dispense volatile material every twenty minutes. In yet another example, control may monitor the current time period continuously or periodically during the blocks 88, 90, as described above. Consequently, control may remain in the blocks 88, 90 for the duration of the shorter time period, e.g., two hours, or until the current period has elapsed before looping back to the block 82. In yet another example intended without limitation, the sensor can be deactivated during the blocks 84, 88, 90 to prevent further sensor activation during such blocks and to conserve power.

Figure 5:
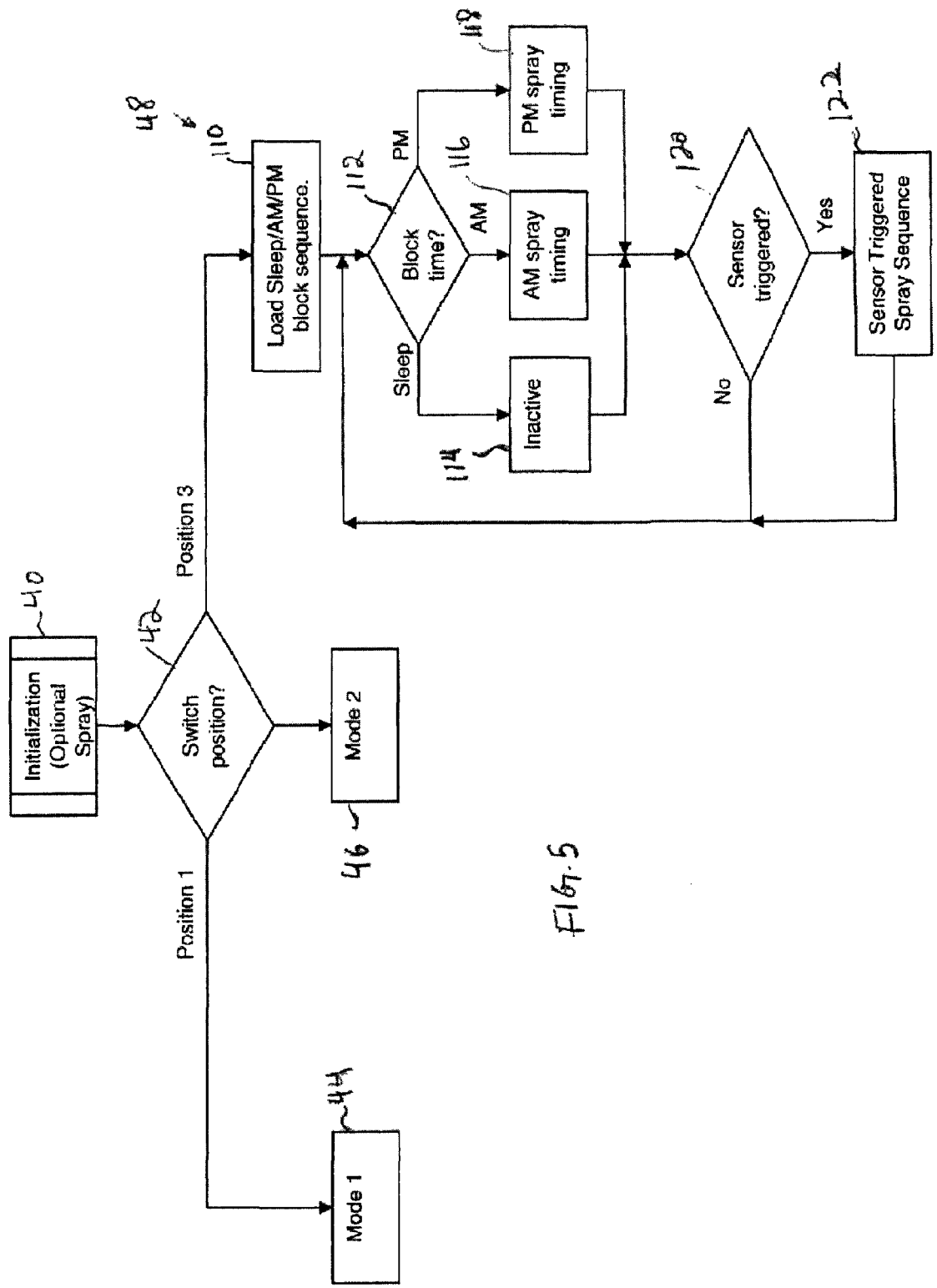
FIG. 5 is a flowchart that illustrates one embodiment of programming according to Mode 3 of FIG. 1.

Referring now to FIG. 5, Mode 3 begins at a block 110, which loads a Sleep/AM/PM block sequence, similarly to the block 60 of FIG. 3 and the block 80 of FIG. 4. For example, the Sleep/AM/PM block sequence loaded by the block 110 may include the same or different time periods and/or spray timings as the examples discussed above. In one non-limiting example, the Sleep sequence time period can be set to between 12:00 AM and 6:00 AM, during which the device 10 is in an inactive state and no volatile is dispensed. The AM sequence time period can be set to between 6:01 AM and 3:00 PM, during which period the device 10 can be controlled to actuate the first container 22 according to an AM spray timing to dispense volatile material once every forty minutes. Further, the PM sequence time period can be set to between 3:01 PM and 11:59 PM, during which period the device 10 can be controlled to actuate the second container 24 according to a PM spray timing to dispense volatile material once every forty minutes.

Following the block 110, control passes to a block 112 to determine the current time period, e.g., the Sleep sequence time period between 12:00 AM and 6:00 AM, the AM sequence time period between 6:01 AM and 3:00 PM, or the PM sequence time period between 3:01 PM and 11:59 PM. If the current time period is the Sleep period, control passes to a block 114 and the device 10 is controlled according to the inactive state where no volatile is dispensed. If the current time period is the AM period, control passes to a block 116 and the device 10 is controlled according to the AM spray timing to dispense the volatile material from the first container 22 once every forty minutes. Similarly, if the current time period is the PM period, control passes to a block 118 and the device 10 is controlled according to the PM spray timing to dispense volatile material from the second container 24 once every forty minutes.

Concurrently while executing the blocks 114, 116, and 118 control loops to the block 120 to determine whether a sensor has been triggered, e.g., the sensor 14 of FIG. 1, which can be a motion sensor that is triggered by detecting motion, a pressure sensor that is triggered by a user pressing on the pressure sensor, or any other type of sensor that would be apparent to one of ordinary skill. If the sensor has not been triggered, control loops back to the block 112 to monitor the current time period and resume execution of the blocks 114, 116, 118 until the current time period expires and/or the sensor is triggered. If the sensor has been triggered, control passes to a block 122 and a spray sequence is performed. In one non-limiting example, the spray sequence of the block 122 includes actuating one or both of the containers 22, 24 once every twenty minutes for a total of six actuations. In the present example, during the block 122, control waits for twenty minutes before the first actuation. Consequently, control remains at the block 122 for two hours. In another example, control immediately actuates one or both of the containers 22, 24 when the sensor is triggered. In yet another example, a container 22, 24 is selected to be actuated during the block 122 based on the current block time. More particularly, if the current block time is the AM time period then the first container 22 is actuated, if the current block time is the PM time period then the second container 24 is actuated, and if the current block time is the sleep period, then either no container is actuated or one or both of the containers can be actuated. After the sixth actuation of the block 122, control passes back to the block 112 to resume operation as discussed above. Control may remain in the block 122 for the duration of the spray sequence, e.g., all six actuations. Alternatively, during the block 122, control may continuously or periodically monitor the current time period and immediately loop back to the decision block 112 if the current time period elapses, similarly to the examples discussed above with reference to FIG. 4.

In further non-limiting examples, control may remain at the block 122 for a delay period, e.g., twenty minutes, before returning to the block 112. Further, control may remain in the blocks 114, 116, and/or 118 for a lockout period, e.g., ten minutes, before passing to the block 120 to monitor the sensor. Still further, during the blocks 114 and/or 122, the sensor can be deactivated to conserve power. In yet another example, if the current time period is the Sleep period, control may pass to the block 114 and then directly back to the decision block 112, thereby, bypassing the blocks 120 and 122.

Various modifications can be made to the flowcharts described hereinabove, without departing from the spirit of the present disclosure. For example, the flowcharts can be modified to include fewer or additional processes, such as, activating the indicator 26, which can be an LED, to flash every ten seconds when the device 10 is not actuating the containers 22, 24 and is not monitoring a sensor, to flash every five seconds when the device is not actuating the containers and is monitoring a sensor, and/or to flash three times prior to actuation of the containers. Further, the time periods, spray sequences, and number of actuations during each time period and/or spray sequence may also be modified. The flowchart can also be modified to rearrange the sequence of the blocks, e.g., the loading of the Sleep/AM/PM block sequence can be performed during the initialization block 40 or after the block 40 and before the block 42 is performed to determine the operating mode.

Still further, the containers 22, 24 may hold any type of volatile material that is to be dispensed. The volatile may be in any suitable form including liquid or gas. The containers 22, 24 may include a propellant or other compressed gases to facilitate the release thereof. The volatile may be a fragrance or insecticide disposed within a carrier liquid, a deodorizing liquid, a cleaning and/or polishing formulation or the like and may also comprise other actives, such as sanitizers, air fresheners, odor eliminators, mold or mildew inhibitors, insect repellents, and the like, or that have aromatherapeutic properties.

INDUSTRIAL APPLICABILITY

The dispensing device disclosed herein can be controlled to operate in one or more modes to provide an improved user experience with various options for dispensing one or more volatile materials to suit various user preferences.

Numerous modifications to the present invention will be apparent to those skilled in the art in view of the foregoing description. Accordingly, this description is to be construed as illustrative only and is presented for the purpose of enabling those skilled in the art to make and use the invention and to teach the best mode of carrying out same. The exclusive rights to all modifications that come within the scope of the appended claims are reserved.

We claim:

1. A dispensing device, comprising:
    first and second actuators adapted to actuate first and second containers, respectively, to dispense volatile material therefrom; and
    a sensor for detecting an environmental condition,
    wherein in a first period the first and second actuators are inactive, in a second period the first actuator actuates the first container at a first frequency to dispense volatile material therefrom, and in a third period the second actuator actuates the second container at a second frequency to dispense volatile material therefrom, and
    wherein, if the sensor has detected the environmental condition, the first and/or second actuators actuate the first and/or second containers, respectively, during a fourth period at a third frequency.

2. The dispensing device of claim 1, wherein the first and second containers are aerosol containers.

3. The dispensing device of claim 1, wherein the third frequency is greater than the first and second frequencies.

4. The dispensing device of claim 1, wherein during the fourth period the first actuator actuates the first container to dispense volatile material therefrom if the device had been operating in the second period and the second actuator actuates the second container to dispense volatile material therefrom if the device had been operating in the third period.

5. The dispensing device of claim 1, wherein the sensor is a motion sensor.

6. The dispensing device of claim 1, further comprising an input device coupled to a controller to allow a user to modify the first, second, and third periods and the first, second, and third frequencies.

7. The dispensing device of claim 1, wherein, by default, the first period is set between 12:00AM and 6:00 AM, the second period is set between 6:01 AM and 3:00 PM, the third period is set between 3:01 PM and 11:59 PM, the first and second frequencies include one actuation every forty minutes, and the third frequency includes one actuation every twenty minutes for a total of six actuations.

8. The dispensing device of claim 1, wherein the sensor is deactivated during the fourth period.

9. The dispensing device of claim 1, wherein the first, second, and third periods are consecutive time periods within a twenty-four hour period.

10. A dispensing device, comprising:
    first and second actuators adapted to actuate first and second containers, respectively, to dispense volatile material therefrom; and
    a sensor for detecting an environmental condition,
    wherein during a first period the first actuator actuates the first container for a first actuation sequence to dispense volatile material therefrom and during a second period the second actuator actuates the second container for a second actuation sequence to dispense volatile material therefrom, and
    wherein the first and second actuation sequences are performed only if the sensor has detected the environmental condition.

11. The dispensing device of claim 10, wherein during a third period the first and second actuators are inactive.

12. The dispensing device of claim 11, wherein the first and second actuation sequences last for a fourth period.

13. The dispensing device of claim 12, wherein the fourth period is two hours and the first and second actuation sequences include one actuation every twenty minutes for two hours.

14. The dispensing device of claim 11, wherein the sensor is deactivated during the third period and the first and second actuation sequences.

15. The dispensing device of claim 11, wherein the first, second, and third periods are consecutive time periods within a twenty-four hour period.

16. The dispensing device of claim 10, wherein the first and second actuation sequences are interrupted if the first or second periods, respectively, elapse.

17. The dispensing device of claim 10, wherein the first and second containers are aerosol containers.

18. The dispensing device of claim 10, wherein the sensor is a motion sensor.

* * * * *